United States Patent [19]

Hisamoto et al.

[11] Patent Number: 4,559,179

[45] Date of Patent: Dec. 17, 1985

[54] FLUORINE-CONTAINING VINYL COMPOUND

[75] Inventors: Iwao Hisamoto, Osaka; Chiaki Maeda, Kyoto; Masaru Hirai, Osaka, all of Japan

[73] Assignee: Daikan Kogyo Co., Ltd., Osaka, Japan

[21] Appl. No.: 596,901

[22] Filed: Apr. 5, 1984

[30] Foreign Application Priority Data

Apr. 12, 1983 [JP] Japan ................... 58-64222

[51] Int. Cl.$^4$ ............................................. C07C 143/68
[52] U.S. Cl. ............... 260/456 F; 526/292.3; 526/292.9; 560/223; 560/254; 560/262; 560/166; 568/610; 568/615
[58] Field of Search ............... 260/456 F; 560/166, 560/223, 254, 262; 568/610, 615

[56] References Cited

U.S. PATENT DOCUMENTS

| | | |
|---|---|---|
| 3,660,360 | 5/1972 | Ray-Chaudhuri .................. 560/223 |
| 4,080,507 | 3/1978 | Gresham .......................... 560/223 |
| 4,472,294 | 9/1984 | Hisamoto .......................... 568/615 |

FOREIGN PATENT DOCUMENTS

| | | | |
|---|---|---|---|
| 2062817 | 6/1972 | Fed. Rep. of Germany ....... 560/223 |
| 42-15083 | 8/1967 | Japan ................................. 560/223 |
| 50-52019 | 5/1975 | Japan ................................. 560/223 |
| 58-194839 | 11/1983 | Japan ................................ 560/223 |
| 1354138 | 5/1974 | United Kingdom ................ 568/615 |

OTHER PUBLICATIONS

"The Condensed Chemical Dictionary", 8th Ed., Revised by Hawley, pp. 367, 646 and 736, (1971).

Primary Examiner—Michael L. Shippen
Attorney, Agent, or Firm—Birch, Stewart, Kolasch & Birch

[57] ABSTRACT

A fluorine-containing vinyl compound of the formula:

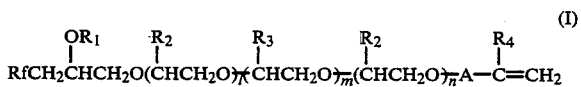

(I)

wherein Rf is fluoroalkyl of 4 to 20 carbon atoms, $R_1$ is hydrogen or acyl of 1 to 3 carbon atoms, one of $R_2$ and $R_3$ is hydrogen and the other is methyl, $R_4$ is hydrogen or methyl, A is a divalent organic group, and l, m and n are each an integer of 0 to 40 and satisfy $0 < l+m+n \leq 40$, which can modify surface properties of resins.

6 Claims, No Drawings

FLUORINE-CONTAINING VINYL COMPOUND

FIELD OF THE INVENTION

The present invention relates to a novel fluorine-containing vinyl compound. More particularly, it relates to a fluorine-containing vinyl compound which can modify surface properties of resins or resin compositions, a process for preparing the same and a polymer comprising the same.

BACKGROUND OF THE INVENTION

Compounding of a fluorine-containing compound such as a fluoroalkyl group containing compound as a modifier in resins or resin compositions improves their surface properties such as non-tackiness, leveling property, antistatic property, stainproofness, non-fogging property, water- and/or oil-repellency etc.

Widely used fluorine-containing compounds as the modifier are of single molecular type. Recently, polymers containing polyalkylene oxide group are also used as the modifier. One example of such the polymers is a copolymer of a fluorine-containing monomeric compound having a polyfluoroalkyl group and a polymerizable functional group (eg. a vinyl group) and a monomeric compound having a polyoxyalkylene group and a vinyl group.

The polymers can modify or improve the surface properties as described above to a certain degree by appropriately selecting kinds and proportion of the fluorine-containing compound and the compound copolymerizable therewith. However, the improvement of the surface properties is not practically satisfied.

As a result of the extensive study to find a good modifier of the surface properties of the resins or the resin compositions, it has now been found that a vinyl compound having both a polyfluoroalkyl group and a polyoxyalkylene group improves the surface properties greatly.

SUMMARY OF THE INVENTION

According to one aspect of the invention, there is provided a fluorine-containing vinyl compound of the formula:

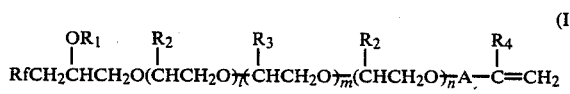

wherein Rf is fluoroalkyl of 4 to 20 carbon atoms, $R_1$ is hydrogen or acyl of 1 to 3 carbon atoms, one of $R_2$ and $R_3$ is hydrogen and the other is methyl, $R_4$ is hydrogen or methyl, A is a divalent organic group, and l, m and n are each an integer of 0 to 40 and satisfy $0 < l+m+n \leq 40$.

According to another aspect of the invention, there is provided a process for preparing the fluorine-containing compound (I) comprising reacting a fluorine-containing epoxide of the formula:

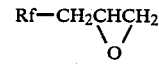

wherein Rf is the same as defined above and a compound of the formula:

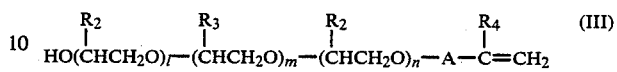

wherein $R_2$, $R_3$, $R_4$, A, l, m and n are the same as defined above, preferably in the presence of a catalyst, to obtain a compound of the formula:

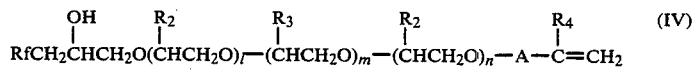

wherein Rf, $R_2$, $R_3$, $R_4$, A, l, m and n are the same as defined above, and optionally esterifying the compound (IV) to obtain a vinyl compound (I) wherein $R_1$ is acyl of 1 to 3 carbon atoms.

According to further aspect of the invention, there is provided a polymer comprising monomeric units derived from the vinyl compound (I).

DETAILED DESCRIPTION OF THE INVENTION

In the compound (I), Rf usually have 4 to 20 carbon atoms, preferably 6 to 15 carbon atoms, more preferably 8 to 12 carbon atoms.

Specific examples of the divalent organic group A are divalent aliphatic groups aush as $-(CH_2)_p-$ in which p is an integer of 1 to 3 carbon atoms (eg. $-CH_2-$, $-CH_2CH_2-$, etc), divalent aromatic groups such as a group of the formula:

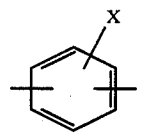

in which X is hydrogen or alkyl having 1 to 4 carbon atoms (eg. phenylene), $-CO-$, $-NHCO-$, $-SO_2-$, etc.

Specific examples of the vinyl compound (I) are as follows:

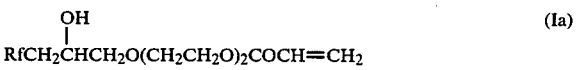  (Ia)

  (Ib)

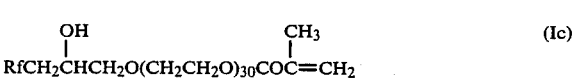  (Ic)

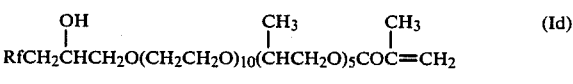  (Id)

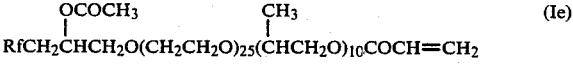  (Ie)

-continued

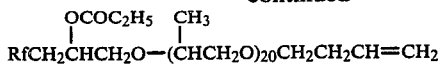 (If)

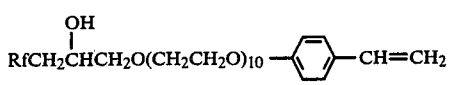 (Ig)

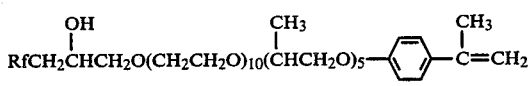 (Ih)

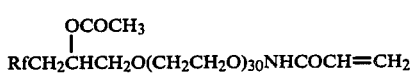 (Ii)

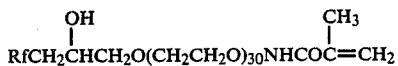 (Ij)

Usually, the reaction of the compounds (II) and (III) is carried out at a temperature of from 40° to 100° C., preferably 50° to 80° C. As the catalyst, an acidic catalyst (eg. BF$_3$-ether complex, AlCl$_3$, ZnCl$_2$, Zn(NO$_3$)$_2$, etc.) is used and among them, BF$_3$-ether complex is preferred. The amount of the catalyst is usually from 0.01 to 2% by weight on the basis of the weight of the fluorine-containing epoxide (II).

After the reaction of the compounds (II) and (III) is completed, the compound (IV) is esterified with a corresponding carboxylic anhydride or carboxylic acid halide (eg. carboxylic acid chloride) according to a per se conventional method. Esterification may be carried out in the absence of a catalyst at a temperature of 10° to 80° C., preferably 30° to 50° C.

The vinyl compound (I) according to the invention is as such used as the modifier of the resin surface.

When the vinyl compound (I) is used in an aqueous system, it has preferably no propylene oxide or more ethylene oxide than propylene oxide in the molecule, because of its better solubility in water. More desirable compound (I) is one in that l+m+n is not less than 2, preferably not less than 4.

When the vinyl compound (I) is used in an organic solvent system, particularly in a non-polar solvent such as petroleum oil, it has no ethylene oxide or more propylene oxide than ethylene oxide in the molecule because of its better solubility to the organic solvent.

When the improvement of the leveling property of the surface is intended, the vinyl compound having both ethylene oxide and propylene oxide (namely m is at least one and at least one of l and n is at least one) provides better effect.

When the improvement of the non-fogging property is intended, advantageously, at least 80% of R$_2$ and R$_3$ is hydrogen.

The vinyl compound (I) in which the group A is —CO— is advantageously used for generally used resins such as acrylic resin, epoxy resin, urethane resin, polyvinyl chloride resin and phenol resin, since it has good compatibility with them. Further, the vinyl compound (I) in which the group A is

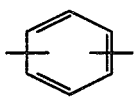

is advantageously used with non-polar resins such as polyolefins (eg. polyethylene and polypropylene), polystyrene, etc.

As discussed above, the groups in the formula (I) may be appropriately selected in accordance with the objects and/or the kind of the resin to be modified by the vinyl compound (I).

Although the vinyl compound (I) may be used as such as discussed in the above, it may be used in the form of a homopolymer or a copolymer with at least one other comonomer in order to improve its effect and its durability.

The polymerization or copolymerization of the vinyl compound (I) may be carried out by a per se conventional manner such as solution polymerization, emulsion polymerization, bulk polymerization, etc.

The polymerization or copolymerization conditions are easily selected by those skilled in art according to the conventional polymerization of known vinyl compounds.

For example, the reaction temperature is from 40° to 80° C., preferably from 50° to 70° C. In the solution and emulsion polymerization, a solvent such as ethanol, isopropanol, ethyl acetate, trichloroethane, methyl ethyl ketone and dimethylformamide is preferably used. As an emulsifier in the emulsion polymerization, polyethyleneglycol and nonyl phenol ether are preferably used. As an initiator, a conventional radical initiator such as an organic or inorganic peroxide (eg. tert-butyl peroxypivarate, tert-butyl 2-ethylhexanoate, etc.), an azo compound (eg. 2,2'-azobisisobutyronitrile, etc.) may be used. The polymerization or copolymerization may be initiated by light or heat.

Specific examples of the comonomer to be copolymerized with the vinyl compound (I) are unsaturated carboxylic acids (eg. acrylic acid, methacrylic acid, etc.), unsatureted carboxylates (eg. methyl acrylate, 2-ethylhexyl acrylate, polyethylene glycol monoacrylate, polyethylene diacrylate, aminoethyl acrylate, polypropylene monoacrylate, polyethylene polypropylene monoacrylate, methyl methacrylate, hydroxyethyl methacrylate, dimethylaminoethyl methacrylate, polyethylene monomethacrylate, polypropylene monomethacrylate, glycidyl methacrylate, etc.), unsaturated carboxylic acid amides (eg. acryl amide, methylolacryl amide, etc.), styrene, alpha-methylstyrene, divinyl benzene, vinyl alcohol, vinyl ether (eg. methyl vinyl ether, ethyl vinyl ether, etc.), acrylonitrile, methacrylonitrile, vinyl amine, vinyl chloride. Other vinyl monomers may be suitably used.

The modification of the resin surface may be effected by coating the surface with a solution of the vinyl compound (I) or its homo- or copolymer in an appropriate solvent. Specific examples of the solvent are halogenated solvents (eg. trichlorotrifluoroethane, tetrachlorodifluoroethane, tetrachloromethane, trichloroethane, etc.)

Alternatively or in addition to the coating, the vinyl compound (I) or its homo- or copolymer may be compounded in the resin or in the resin composition by adding it in the solution of the resin or kneading it together with the resin or the resin composition in a melt state. The amount of the vinyl compound (I) or its homo- or copolymer to be compounded varies with the kinds of the compound (I) and/or of the resin to be modified. Usually, it is from 0.001 to 2% by weight.

PREFERRED EMBODIMENTS OF THE INVENTION

The present invention will be hereinafter explained further in detail by following Examples.

EXAMPLE 1

In a 200 ml flask equipped with a thermometer, a condenser and a stirrer, $$C_9H_{19}CH_2\underset{O}{\overset{}{CH-CH_2}}$$

(52.6 g, 0.1 mole), $HO(CH_2CH_2O)_{10}COC(CH_3)=CH_2$ (52.6 g, 0.1 mole) and, as a catalyst, $BF_3$-ether complex (0.26 g) were charged and stirred at 70° C. for 8 hours. Analysis by gaschromatography (Column: silicone SE-30, 1 m. Column temperature: raised from 100° C. to 250° C.) confirmed the consumption of the starting material epoxide. A peak at 1,640 cm$^{-1}$ in IR spectrum confirmed the presence of double bonds.

After removing insoluble materials in methanol from the reaction mixture, the resulting product was washed with benzene and dried in vacuo to give, as a transparent viscous liquid, $C_9F_{19}CH_2CH(OH)CH_2O(CH_2CH_2O)_{10}COC(CH_3)=CH_2$ (96.8 g). Yield, 92%. M.P., 10°–15° C. B.P., 200° C./10 mmHg.

Elemental analysis: Calculated: F, 34.3%; C, 41.1%; H, 4.8%, O, 19.8%. Found: F, 33.7%; C, 40.8%; H, 4.9%; O, 20.6%.

EXAMPLE 2

In the same flask as used in Example 1, $$C_8F_{17}CH_2\underset{O}{\overset{}{CH-CH_2}}$$

(47.6 g, 0.1 mole), $HO(CH_2CH_2O)_{10}(CH(CH_3)CH_2O)_5COC(CH_3)=CH_2$ (81.6 g, 0.1 mole) and $BF_3$-ether complex (0.4 g) were charged and stirred at 65° C. for 9 hours. The consumption of the epoxide and the presence of the double bonds were confirmed in the same manner as in Example 1.

After removing insoluble materials in methanol from the reaction mixture, the resulting product was washed with an excess amount of benzene and dried in vacuo to give as a transparent viscous liquid, $C_8H_{17}CH_2CH(OH)CH_2O(CH_2CH_2O)_{10}(CH(CH_3)CH_2O)_5COC(CH_3)=CH_2$ (117.6 g). Yield, 91%. M.P., 8°–12° C. B.P., 200° C./10 mmHg.

Elemental analysis: Calculated: F, 25.0%; C, 46.4%; H, 6.3%, O, 22.3%. Found: F, 24.1%; C, 46.8%; H, 6.3%; O, 22.8%.

EXAMPLE 3

In a 200 ml four-necked flask equipped with a thermometer, a condenser, a stirrer and a nitrogen-inlet tube, the compound obtained in Example 1 (28 g), isopropanol (112 g) and dodecyl mercaptan (0.4 g) were charged and stirred at 67° C. for 30 minutes under a nitrogen stream. Then, as a polymerization initiator, perbutyl pivalate (0.17 g) was added and the polymerization was effected at the same temperature for 6 hours.

Isopropanol was evaporated off. The residue was washed with an excess amount of benzene and dried in vacuo to give a highly viscous liquid (26.1 g). M.P., 25°–30° C. B.P., 200° C./10 mmHg.

An IR spectrum, the peak at 1,640 cm$^{-1}$ corresponding to the double bond of the starting material was disappeared, which confirmed the formation of the polymer.

EXAMPLE 4

In the same flask as used in Example 1, $$C_9H_{19}CH_2\underset{O}{\overset{}{CH-CH_2}}$$

(52.6 g, 0.1 mole), $HO(CH(CH_3)CH_2O)_{10}COC(CH_3)=CH_2$ (66.6 g, 0.1 mole) and $BF_3$-ether complex (0.5 g) were charged and stirred at 65° C. for 8 hours. The consumption of the epoxide and the presence of the double bonds were confirmed in the same manner as in Example 1.

After removing insoluble materials in methanol from the reaction mixture, the resulting product was washed with an excess amount of hexane and dried in vacuo to give as a transparent viscous liquid, $C_9F_{19}CH_2CH(OH)CH_2O(CH(CH_3)CH_2O)_{10}COC(CH_3)=CH_2$ (102.5 g). Yield, 86%. M.P., $-1-+2°$ C. B.P., 200° C./10 mmHg.

Elemental analysis: Calculated: F, 30.2%; C, 46.4%; H, 6.0%, O, 17.4%. Found: F, 29.7%; C, 46.7%; H, 6.1%; O, 17.5%.

EXAMPLE 5

A resin coating composition having following formulation and containing 0.04% by weight of a polymer as shown in Table 1 was spray coated on an aluminum plate (10 cm × 10 cm) and dried at 140° C.

| Formulation | % by weight |
| --- | --- |
| Epoxy resin | 20 |
| Phenol resin | 10 |
| Butanol | 15 |
| Xylene | 40 |
| Cellosolve acetate | 12 |
| Titanium oxide | 3 |

Smoothness of the surface of the coating was examined by naked eyes with reflected natural light and by mirror reflection rate at 60 degrees and evaluated according to the following criteria:
O: good smoothness over the entire surface
Δ: Fairly good smoothness
X: Poor smoothness
The results are shown in Table 1.

TABLE 1

| Polymer | Smoothness |
| --- | --- |
| None | X |
| Homopolymer of $C_{11}F_{23}CH_2\overset{OH}{\underset{|}{C}H}CH_2O(CH_2CH_2O)_2COCH=CH_2$ | Δ |

TABLE 1-continued

| Polymer | Smoothness |
|---|---|
| Homopolymer of<br><br>$\quad\quad\quad\quad\text{OH}\quad\quad\quad\quad\quad\text{CH}_3\quad\quad\quad\text{CH}_3$<br>$\quad\quad\quad\quad\;\|\quad\quad\quad\quad\quad\quad\;\|\quad\quad\quad\quad\;\|$<br>$\text{C}_9\text{F}_{19}\text{CH}_2\text{CHCH}_2\text{O}(\text{CH}_2\text{CH}_2\text{O})_{10}(\text{CHCH}_2\text{O})_5\text{COC}=\text{CH}_2$ | O |
| Copolymer of<br><br>$\quad\quad\quad\quad\text{OH}\quad\quad\quad\quad\quad\text{CH}_3\quad\quad\quad\quad\quad\quad\quad\quad\text{CH}_3$<br>$\quad\quad\quad\quad\;\|\quad\quad\quad\quad\quad\quad\;\|\quad\quad\quad\quad\quad\quad\quad\quad\;\|$<br>$\text{C}_{13}\text{F}_{27}\text{CH}_2\text{CHCH}_2\text{O}(\text{CH}_2\text{CH}_2\text{O})_{10}(\text{CHCH}_2\text{O})_5\text{—C}_6\text{H}_4\text{—C}=\text{CH}_2$<br><br>and<br><br>$\quad\quad\quad\quad\quad\quad\quad\quad\quad\quad\text{CH}_3$<br>$\quad\quad\quad\quad\quad\quad\quad\quad\quad\quad\;\|$<br>$\text{CH}_3\text{O}(\text{CH}_2\text{CH}_2\text{O})_8\text{COC}=\text{CH}_2$ (weight ratio of 2:1) | O |

EXAMPLE 6

A base film of acetate resin was dipped in a 0.01% by weight solution of a polymer shown in Table 2 in trichlorotrifluoroethane and dried in the air to form a polymer film on the base film. Frictionally charged voltage on the film was measured by means of a Kyoto University-type rotary static tester using polytetrafluoroethylene as a frictional belt. The results are shown in Table 2.

TABLE 2

| Polymer | Frictionally charged voltage (Volts) |
|---|---|
| None | 2,000 |
| Homopolymer of<br><br>$\quad\quad\quad\quad\text{OH}\quad\quad\quad\quad\quad\text{CH}_3$<br>$\quad\quad\quad\quad\;\|\quad\quad\quad\quad\quad\quad\;\|$<br>$\text{C}_8\text{F}_{17}\text{CH}_2\text{CHCH}_2\text{O}(\text{CH}_2\text{CH}_2\text{O})_{30}\text{COC}=\text{CH}_2$ | 120 |
| Homopolymer of<br><br>$\quad\quad\quad\quad\text{OCOCH}_3$<br>$\quad\quad\quad\quad\;\|$<br>$\text{C}_6\text{F}_{13}\text{CH}_2\text{CHCH}_2\text{O}(\text{CH}_2\text{CH}_2\text{O})_{30}\text{NHCOCH}=\text{CH}_2$ | 150 |

EXAMPLE 7

A resin composition was prepared by compounding polyvinyl chloride (100 parts by weight), dioctyl phthalate (44 parts by weight) and, as a anti-drip agent, a sorbitan monostearate/ethylene oxide adduct (one part by weight) and sorbitan monoparmitate (one part by weight) and adding a compound (0.2 part by weight) shown in Table 3 as an anifogging agent. The composition was calender rolled to form a film having a thickness of 0.1 mm. A dome having a diameter of 50 cm and a height of 30 cm was constructed of the thus prepared film, and in the dome, a glass container (20 cm×20 cm×5 cm) filled with water was placed. Room temperature was varied between 5° C. and 30° C. and a degree of fog creation was evaluated according to the following criteria:

O: Fog was not created.
Δ: Fog was slightly created.
X: Fog was densely created.

The results are shown in Table 3.

TABLE 3

| Compound | Evaluation |
|---|---|
| None | X |
| $\quad\quad\quad\quad\text{OH}\quad\quad\quad\quad\quad\text{CH}_3$<br>$\quad\quad\quad\quad\;\|\quad\quad\quad\quad\quad\quad\;\|$<br>$\text{C}_9\text{F}_{19}\text{CH}_2\text{CHCH}_2\text{O}(\text{CH}_2\text{CH}_2\text{O})_{10}\text{COC}=\text{CH}_2$ | O |
| Homopolymer of<br><br>$\quad\quad\quad\quad\text{OH}\quad\quad\quad\quad\quad\text{CH}_3$<br>$\quad\quad\quad\quad\;\|\quad\quad\quad\quad\quad\quad\;\|$<br>$\text{C}_8\text{F}_{17}\text{CH}_2\text{CHCH}_2\text{O}(\text{CH}_2\text{CH}_2\text{O})_{30}\text{NHCOC}=\text{CH}_2$ | Δ |
| Copolymer of<br><br>$\quad\quad\quad\quad\text{OH}$<br>$\quad\quad\quad\quad\;\|$<br>$\text{C}_9\text{F}_{19}\text{CH}_2\text{CHCH}_2\text{O}(\text{CH}_2\text{CH}_2\text{O})_{10}\text{COCH}=\text{CH}_2$<br><br>and<br><br>$\quad\quad\quad\quad\quad\quad\quad\quad\text{CH}_3$<br>$\quad\quad\quad\quad\quad\quad\quad\quad\;\|$<br>$\text{HO}(\text{CH}_2\text{CH}_2\text{O})_{10}\text{COC}=\text{CH}_2$ (weight ratio of 1:3) | O |

What is claimed is:

1. A fluorine-containing vinyl compound of the formula:

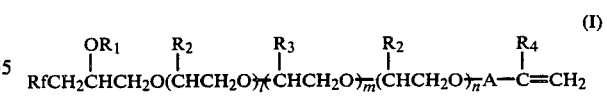

$$\text{RfCH}_2\text{CHCH}_2\text{O}(\text{CHCH}_2\text{O})_{\overline{l}}(\text{CHCH}_2\text{O})_{\overline{m}}(\text{CHCH}_2\text{O})_{\overline{n}}\text{A—C}=\text{CH}_2 \quad\quad (I)$$

with substituents $\text{OR}_1$, $\text{R}_2$, $\text{R}_3$, $\text{R}_2$, $\text{R}_4$ wherein Rf is perfluoroalkyl of 4 to 20 carbon atoms, $R_1$ is hydrogen, —COH, —COCH$_3$, or —COC$_2$H$_5$, one of $R_2$ and $R_3$ is hydrogen and the other is methyl, $R_4$ is hydrogen or methyl, A is selected from the group consisting of an aliphatic or aromatic divalent group, CO and SO$_2$ and l, m and n are each an integer of 0 to 40 and satisfy $0 < l+m+n \leq 40$.

2. A fluorine-containing vinyl compound according to claim 1, wherein the group A is one selected from the group consisting of —(CH$_2$)$_p$— in which p is an integer of 1 to 3, a group of the formula:

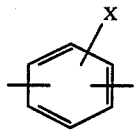

in which X is hydrogen or alkyl of 1 to 4 carbon atoms, —CO—, and —SO$_2$—.

3. A fluorine-containing vinyl compound according to claim 1, wherein m is at least 1, and at least one of l and n is at least one.

4. A fluorine-containing vinyl compound according to claim 1, wherein Rf has 6 to 15 carbon atoms.

5. A fluorine-containing vinyl compound according to claim 1, which has more ethyleneoxy than propyleneoxy.

6. A fluorine-containing vinyl compound according to claim 1, which has more propyleneoxy than ethyleneoxy.

* * * * *